(12) United States Patent
Viola

(10) Patent No.: US 8,678,263 B2
(45) Date of Patent: Mar. 25, 2014

(54) MATERIALS DELIVERY SYSTEM FOR STAPLING DEVICE

(75) Inventor: Frank J. Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 610 days.

(21) Appl. No.: 12/203,261

(22) Filed: Sep. 3, 2008

(65) Prior Publication Data

US 2009/0078739 A1    Mar. 26, 2009

Related U.S. Application Data

(60) Provisional application No. 60/995,024, filed on Sep. 24, 2007.

(51) Int. Cl.
*A61B 17/068* (2006.01)

(52) U.S. Cl.
USPC ............... 227/175.1; 227/176.1; 227/180.1

(58) Field of Classification Search
USPC ............ 227/180.1, 181.1, 178, 175.1, 176.1; 606/186; 604/57, 58, 265, 533, 396, 604/305
See application file for complete search history.

(56) References Cited

U.S. PATENT DOCUMENTS

| | | | |
|---|---|---|---|
| 4,576,591 A * | 3/1986 | Kaye et al. | 604/62 |
| 6,488,197 B1 | 12/2002 | Whitman | |
| 6,491,201 B1 | 12/2002 | Whitman | |
| 2003/0009193 A1 | 1/2003 | Corsaro | |
| 2003/0097103 A1 * | 5/2003 | Horney et al. | 604/369 |
| 2005/0145671 A1 | 7/2005 | Viola | |
| 2005/0184121 A1 * | 8/2005 | Heinrich | 227/175.1 |
| 2005/0230453 A1 | 10/2005 | Viola | |
| 2006/0085032 A1 | 4/2006 | Viola | |
| 2006/0085033 A1 | 4/2006 | Criscuolo et al. | |
| 2006/0108393 A1 | 5/2006 | Heinrich et al. | |
| 2006/0111738 A1 * | 5/2006 | Wenchell | 606/186 |
| 2007/0034667 A1 | 2/2007 | Holsten et al. | |
| 2007/0185463 A1 * | 8/2007 | Mulligan | 604/305 |
| 2008/0085296 A1 * | 4/2008 | Powell et al. | 424/423 |
| 2008/0110958 A1 * | 5/2008 | McKenna et al. | 227/176.1 |

FOREIGN PATENT DOCUMENTS

| | | |
|---|---|---|
| EP | 1754445 | 2/2007 |
| WO | 0162158 | 8/2001 |
| WO | 03094743 | 11/2003 |
| WO | 03094746 | 11/2003 |
| WO | WO 03094746 A1 * | 11/2003 |

* cited by examiner

*Primary Examiner* — Thanh Truong
*Assistant Examiner* — Nathaniel Chukwurah

(57) ABSTRACT

There is disclosed a materials delivery system for use with a surgical stapling instrument having at least one jaw including a knife slot. The materials delivery system includes a series of treatment material receiving pockets positioned adjacent the knife slot such that a portion of each pocket is open to the knife slot. A source of treatment material is positioned within the pockets such that passage of the knife blade adjacent to the pockets repeatedly coats the knife blade with the treatment material.

17 Claims, 7 Drawing Sheets

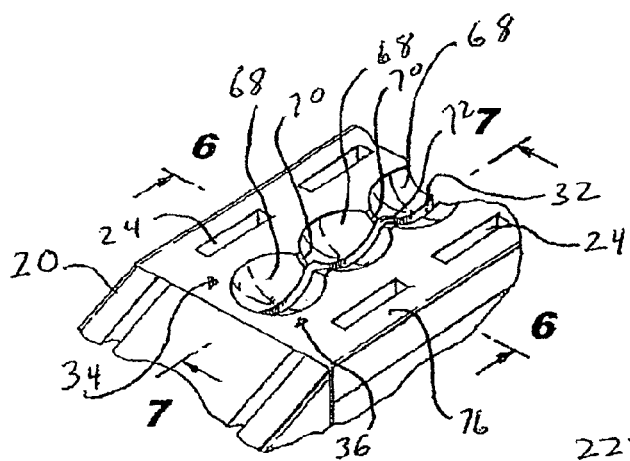
Fig. 4
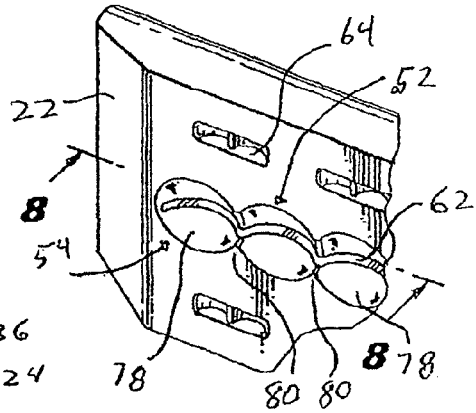
Fig. 5
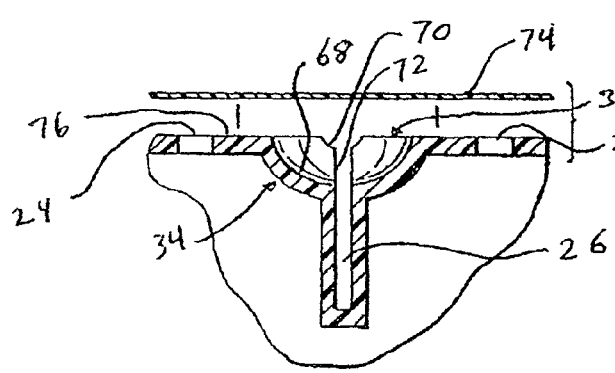
Fig. 6
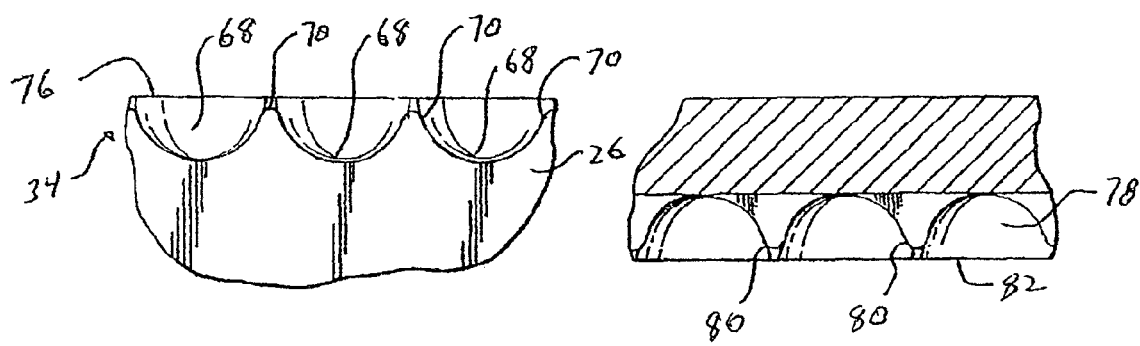
Fig. 7 Fig. 8

MATERIALS DELIVERY SYSTEM FOR STAPLING DEVICE

CROSS-REFERENCE TO RELATED APPLICATIONS

This application claims the benefit of and priority to U.S. Provisional Patent Application No. 60/995,024, filed Sep. 24, 2007, the entire disclosure of which is incorporated by reference herein.

BACKGROUND

1. Technical Field

The present disclosure relates to materials delivery systems for use in surgical instruments having a knife blade. More particularly, the present disclosure relates to systems for repeatedly resupplying or recoating a knife blade with a treatment material as it passes through tissue.

2. Background of Related Art

During various surgical procedures, tissue is grasped by the jaws of a surgical instrument and cut or severed by a knife blade passing through the jaws. Often it is desirable to treat the cut tissues with various materials capable of providing clinical benefits, such as, for example, hemostasis, antimicrobials, etc. These materials are typically available in powder form which can be applied to the knife blade of the surgical instrument as a coating. The powdered coating is then transferred to the tissues as the knife blade passes therethrough.

However, as the knife blade passes through the tissue, the coating is progressively worn off during transfer to tissue. In situations where the knife blade has an extended stroke through the tissue, for example, in a linear stapling device, the coating may be depleted as the knife stroke continues, providing inadequate application of material, and may even become completely worn off prior to the end of the knife blade stroke leaving later areas of tissue untreated.

Thus, it would be desirable to provide a material supply system for use in resupplying treatment material to the knife blade of a surgical instrument as the knife blade passes through tissue grasped between jaws of the surgical instrument. It would be further desirable to provide a material supply system for use in resupplying treatment material to a knife blade of a linear stapling device.

SUMMARY

There is disclosed a material(s) delivery system of a surgical instrument having a longitudinally extending knife slot. The delivery system generally includes at least one, and preferably a series of, pockets positioned adjacent the knife slot such that a portion of each pocket is open to the knife slot and a source of treatment material is positioned within the series of pockets.

In one embodiment, the series of pockets are positioned along one side of the knife slot while in an alternative embodiment a series of pockets is positioned on opposite sides of the knife slot.

The series of pockets preferably comprises an alternating series of depressions and hills formed in the jaw adjacent the knife slot. Each of the depressions preferably has a semispherical configuration. The jaw is formed with a tissue contacting face surface and the tops of the hills preferably lie below the level of the tissue contacting face surface.

In a particular embodiment, the depressions are positioned on a first side of the knife slot and are laterally aligned with hills positioned on a second side of the knife slot.

In one embodiment, the source of treatment material is a series of plugs interconnected by stems. In an alternative embodiment, the source of treatment material includes a pair or series of plugs interconnected by stems and defining a channel therebetween for passage of the knife blade. In a still further alternative embodiment, the source of treatment material includes a series of unconnected plugs positioned within the pockets.

In particular embodiments, the treatment material is a powder while in alternative embodiments the treatment material is a gel or paste or fluid or other material.

The disclosed treatment material delivery system may additionally include a membrane or buttress material positioned over the pockets.

In a specific embodiment, the instrument includes a jaw wherein the at least one pocket is in the jaw and the jaw is a staple cartridge having a plurality of staple containing slots. In another embodiment, the jaw is an anvil having a plurality of staple clinching pockets.

There is also disclosed a surgical stapling device including a handle having an actuation trigger and an elongate tubular member extending distally from the handle. A jaw assembly is positioned on a distal end of the elongate tubular member and includes first and second jaws movably mounted relative to each other. Each of the first and second jaws has a longitudinally extending knife slot formed therein. The surgical stapling device further includes a series of pockets formed in at least one of the first and second jaws and adjacent the knife slots such that a portion of each pocket is open to the knife slots. In one embodiment, a source of treatment material is contained in the pockets.

Preferably, the series of pockets is formed in both the first and second jaws. Preferably, the series of pockets includes an alternating series of hills and depressions. In one embodiment, the treatment material is a powder.

DESCRIPTION OF THE DRAWINGS

Various embodiments of the presently disclosed material(s) delivery system for use with a surgical stapling are disclosed herein with reference to the drawings, wherein:

FIG. 4 is a partial perspective view of the distal end of the powder containing staple cartridge;

FIG. 5 is a partial perspective view of the distal end of the powder containing anvil;

FIG. 6 is a cross-sectional view taken along line 6-6 of FIG. 4;

FIG. 7 is a cross-sectional view taken along line 7-7 of FIG. 4;

FIG. 8 is a cross-sectional view taken along line 8-8 of FIG. 5;

DETAILED DESCRIPTION OF EMBODIMENTS

Embodiments of the presently disclosed supply systems for use in a linear surgical stapling device will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
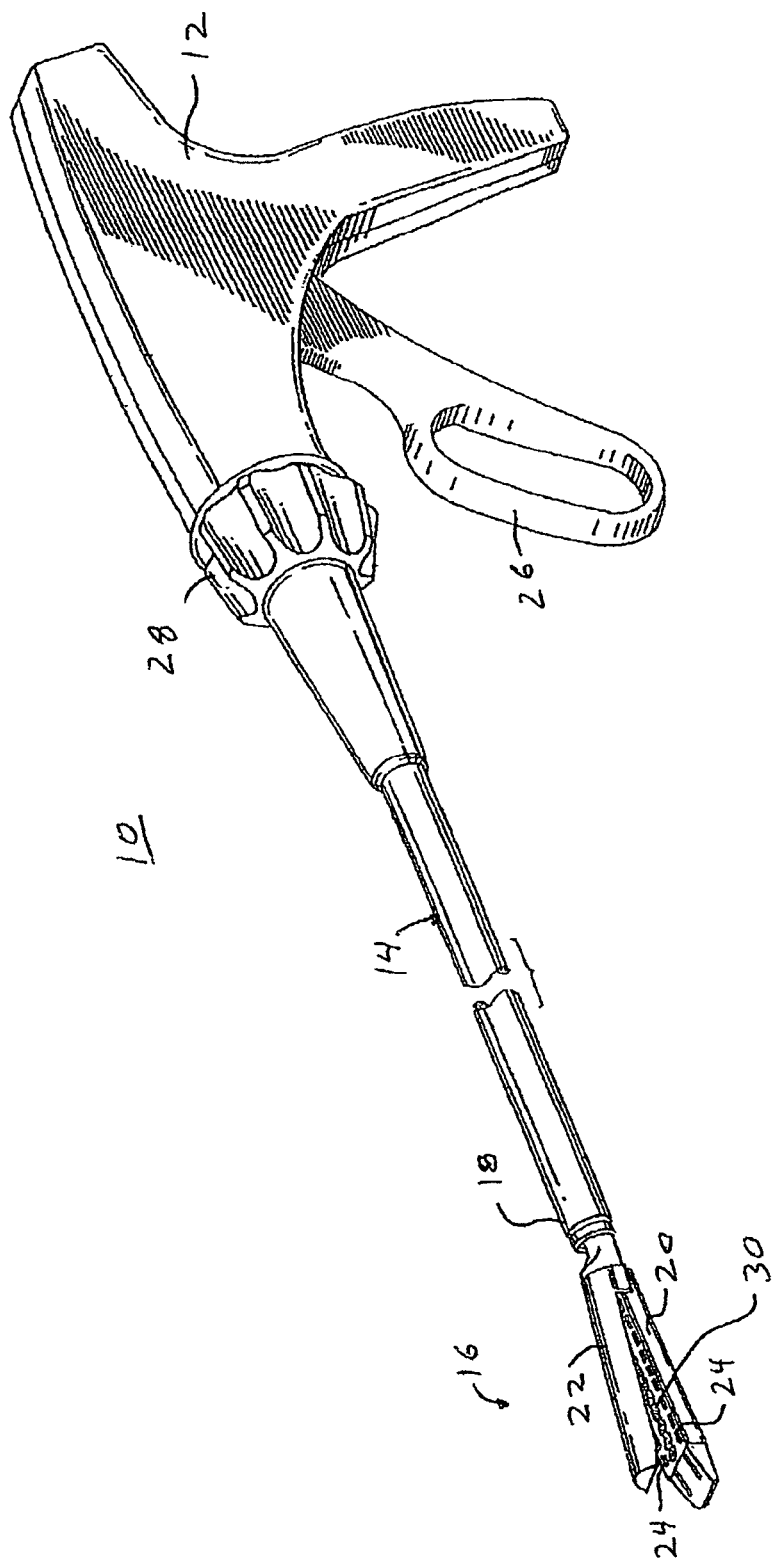
FIG. 1 is a perspective view of a linear surgical stapling device incorporating one embodiment of a material(s) delivery system.

Referring to FIG. 1, there is disclosed a surgical instrument or linear stapling device 10 of the type typically used to apply parallel rows or lines of staples to tissue and to sever the tissue between the applied staple lines. Linear stapling device 10 generally includes a pistol grip style handle 12 having an elongate tubular member 14 extending distally from handle 12. A jaw assembly 16 is mounted on a distal end 18 of elongate tubular member 14 and includes a staple cartridge 20 mounted on distal end 18 and an anvil member 22 movably mounted on distal end 18. Staple cartridge 20 includes parallel rows of staple containing slots 24 for stapling tissue sections together.

A trigger 26 is provided on handle 12 and is initially actuable to move anvil member 22 from an open position spaced apart from staple cartridge 20 to a tissue grasping closed position substantially adjacent staple cartridge 20. Further actuation of trigger 26 operates to eject staples (not shown) positioned in rows of staple containing slots 24 and into tissue. A rotation collar 28 is attached to elongate tubular member 14 to orient jaw assembly 16 relative to tissue being operated on. A cartridge supply system 30 is associated with staple cartridge 20 to supply various treatment materials to tissue as described in more detail hereinbelow.

Figure 2:
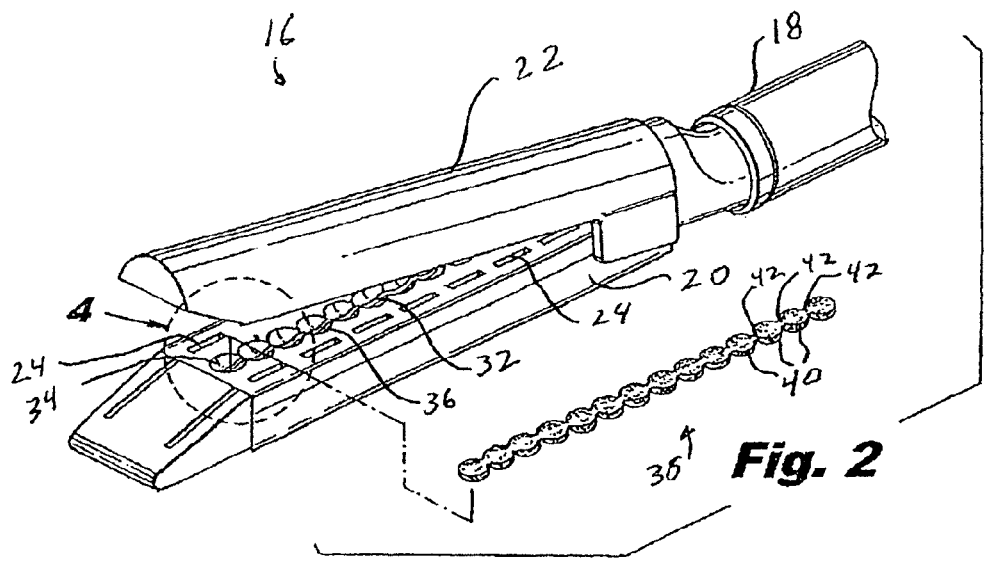
FIG. 2 is an enlarged perspective view of the distal end of the embodiment of FIG. 1 illustrating a powder containing staple cartridge and a powder supply in the form of a powder strip.

Referring now to FIG. 2, staple cartridge is formed with a knife slot along its length and extending between staple containing slots 24. As noted above, knife slot 32 is provided for passage of a knife blade (described below), associated with linear stapling device 10, through tissue and facilitate the application of treatment materials to the cut tissue. Cartridge supply system includes a pair of longitudinally extending combinations of hills and valleys or pockets 34 and 36. Pockets 34 and 36 are mirror images of each other and provide receptacles for receipt of a supply of treatment materials 38 for coating of the knife blade.

In one embodiment, supply of treatment materials 38 is formed as a plurality of interconnected plugs 40 which fill the "valleys" in pockets 34 and 36. Plugs 40 are interconnected by stems 42 which fill the "hills" in pockets 34 and 36 located between the valleys as described in more detail below.

As noted above, supply of treatment material 38 may consist of various materials providing hemostasis, antimicrobial effects, etc. to the cut tissue. When these materials are supplied as a powder, plurality of interconnected plugs 40 and stems 42 may be formed by compressing the powder or otherwise treating the powder in a manner so as to allow it to retain its shape within longitudinal pockets 34 and 36. Passage of the knife blade through knife slot 32, and thus through supply of treatment material 38, fractures the compressed powder and repeatedly coats the knife blade as it travels through knife slot 32.

The treatment material could also be a gel, paste or fluid. Also, the treatment material could be encapsulated in polyethylene or other material, with the encapsulation broken by the knife to expose the treatment material.

Figure 2A:
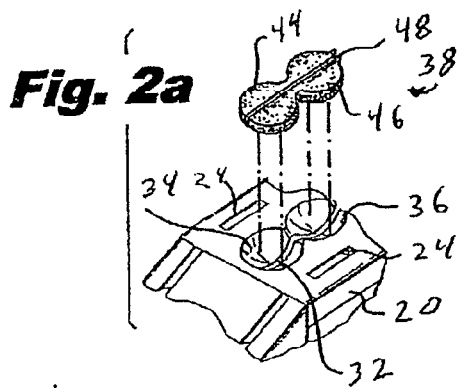
FIG. 2a is a partial perspective view of an alternate embodiment of a powder supply in the form of a split powder strip for use in the powder containing staple cartridge.

Referring for the moment to FIG. 2a, there is disclosed an alternate method of forming supply of treatment material 38. Supply of treatment material 38 may be formed as a longitudinally extending pair of split sides 44 and 46 configured to fit in pockets 34 and 36, respectively. Split sides 44 and 46 define a slot or channel 48 for passage of the knife blade. In this embodiment, passage of the knife blade against the edges of split sides 44 and 46, defining slot 48, wisks or otherwise coats the knife blade without the knife blade having to fracture a compressed powder. This is advantageous where supply of treatment material 38 is of a soft material such as, for example, a gel, etc.

Figure 2B:
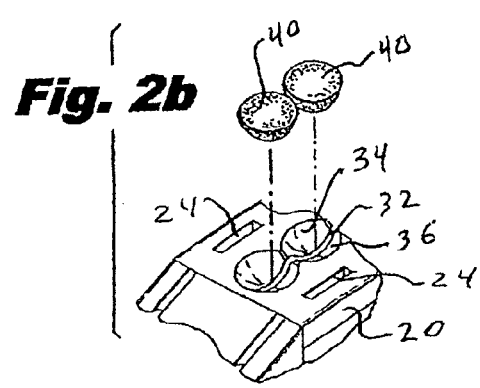
FIG. 2b is partial perspective view of another alternate embodiment of a powder supply in the form of individual powder containing plugs for use in the powder containing staple cartridge.

Referring further to FIG. 2b, there is disclosed another alternative embodiment of supply of treatment material 38. In this embodiment, supply of treatment material 38 may be formed of a series of unconnected plugs 40 which fill the valleys of pockets 34 and 46 without positioning any of the treatment material in the hills separating the valleys.

Figure 3:
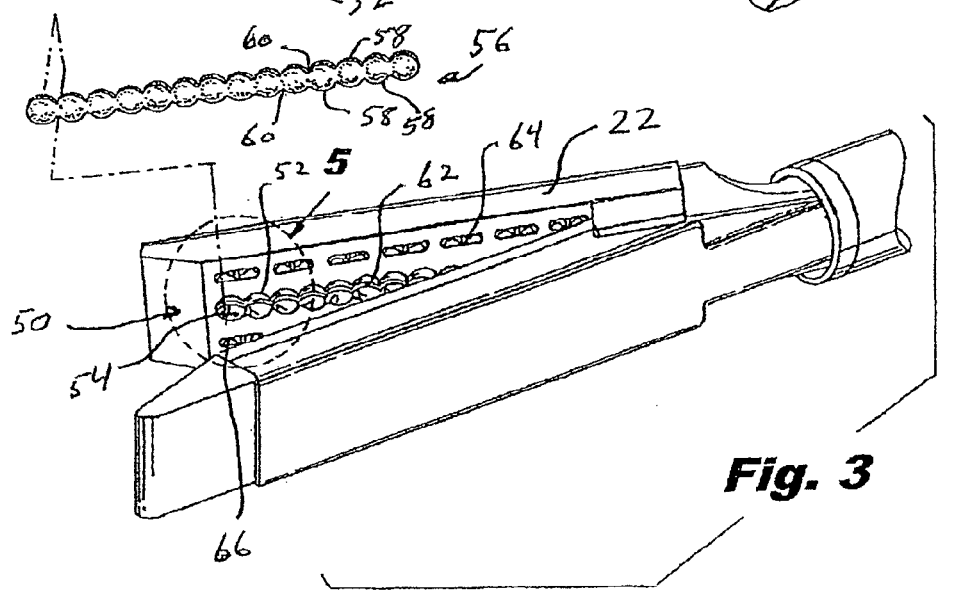
FIG. 3 is an enlarged perspective view of the distal end of the embodiment of FIG. 1, illustrating a powder containing anvil and powder supply.

Turning now to FIG. 3, there is also disclosed a treatment material or anvil supply system 50 associated with anvil member 22. Anvil supply system 50 is substantially identical to cartridge supply system 30 and generally includes a pair of longitudinally extending pockets 52 and 54. Anvil supply system 50 also includes a supply of treatment material 56 formed as a series of interconnected plugs 58 and stems 60. Alternatively, anvil supply system 50 may include other disclosed supplies of treatment material such as split rows of material, unconnected plugs, etc.

Anvil member 22 further includes a knife slot 62 passing between longitudinally extending pockets 52 and 54, similar to that of knife slot 32 described hereinabove with respect to staple cartridge 20. Anvil member 22 additionally includes a pair of longitudinal extending rows of staple clinching pockets 64 and 66 for clinching staples as they pass from staple cartridge 20 through tissue and into anvil member 22.

Referring now to FIGS. 4, 6 and 7, a more detailed description of the configuration of longitudinally extending pockets 34 and 36 in staple cartridge 20 will now be given. Referring initially to FIGS. 4 and 6, and as noted above, pockets 34 and 36 comprise longitudinally extending series of valleys or depressions 68 separated by hills 70. While the following description is given with respect to pockets 34, it is understood that pockets 36 positioned on the opposite side of knife slot 32 are identical to, and mirror images of, pockets 34.

Depressions 68 are generally of a semi-spherical shape for receipt of supply treatment material 38. As best shown in FIG. 6, a side wall 72 of hills 70 forms a common side wall with knife slot 26. Thus, when supply of treatment material 38 (not shown) is positioned within depressions 68, treatment material 38 is exposed to the knife as it passes through knife slot 26. This allows the knife blade to scrape or rub off a portion of supply of treatment material 38 as it passes depressions 68. Depressions 68 thus serve as reservoirs for a supply of treatment material 38.

The tops of the hills 70 preferably lie below the level of the tissue contacting face surface of the cartridge however alternatively they can be substantially flush or protrude slightly past the surface.

With specific reference to FIG. 6, a retention sheet or membrane 74 may be provided to facilitate retention of supply of treatment material 38 within depressions 68. Membrane 74 may be removed prior to use of linear stapling device 10 or maybe left in place to be severed as the knife blade passes through knife slot 26. Alternatively, membrane 74 may be formed from a buttress material to be stapled to tissue.

Referring to FIGS. 4, 6 and 7, and as best shown in FIG. 7, the tops of hills 70 are positioned slightly below a surface face 76 of staple cartridge 20. This provides room or space for stems 42 of supply of treatment material 38 to remain slightly below or flush with surface face 72 of staple cartridge 20 and avoid interference with any tissue captured between staple cartridge 20 and anvil number 22. With continued reference to FIG. 7, while pockets 34 are shown as semi-spherical depressions 68 interspersed by hills 70, pockets 34 may be configured to have slightly smoother transitions between adjacent depressions 68 such that pockets 34 assume a more sinusoidal configuration.

Referring now to FIGS. 5 and 8, the configurations of pockets 52 and 54 formed in anvil 22 are substantially identical in configuration to pockets 34 and 36 formed in staple cartridge 20. For example, pockets 52 consist of depressions 78 interspersed by hills 80 similar to that of depressions 68 and hills 70 described hereinabove with respect to staple cartridge 20. Thus, depressions 78 are also semi-spherical in configuration and hills 80 preferably lie below a surface face 82 of anvil 22. With specific reference to FIG. 8, the transitions between adjacent depressions 78 may be formed to assume a more sinusoidal configuration to assist in allowing flow of supply of treatment material 56 (not shown) between adjacent depressions 78.

Figure 9:
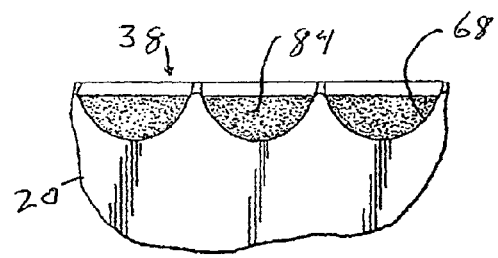
FIG. 9 is a cross-sectional view similar to FIG. 7 illustrating powder valleys of the powder containing staple cartridge filled with powder.
Figure 10:
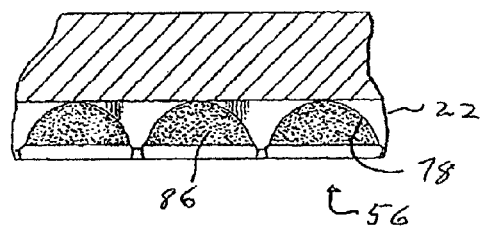
FIG. 10 is a cross-sectional view similar to FIG. 8 illustrating powder valleys of the powder containing anvil filled with powder.

As noted hereinabove, supply of treatment materials 38 and 56 may consist of various powders, gels or fluids. Thus, as best shown in the FIGS. 9 and 10, supply of treatment material 38 positioned within depressions 68 of staple cartridge 20 may consist of a powder 84 while supply of treatment material 56 contained within depressions 78 of anvil member 22 may also consist of a powder 86.

Figure 11:
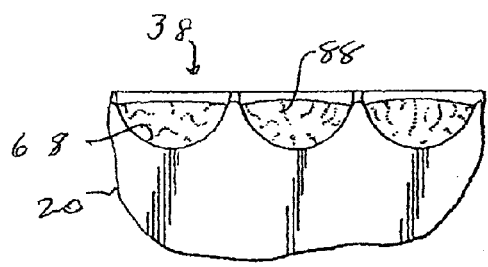
FIG. 11 is a cross-sectional view similar to FIG. 7 illustrating valleys of the staple cartridge filled with a gel.
Figure 12:
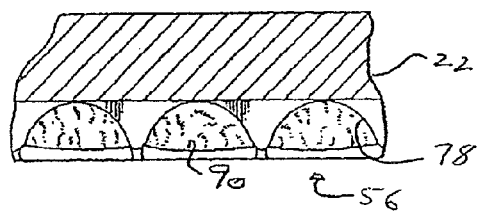
FIG. 12 is a cross-sectional view similar to FIG. 8 illustrating valleys of the anvil filled with a gel.

With reference to FIGS. 11 and 12, in an alternative embodiment, supply of treatment material 38 contained within depressions 68 of staple cartridge 20 may consist of a gel 88. Likewise, supply of treatment material 56 contained within depressions 78 and anvil member 22 my also consist of a gel 90.

Figure 13:
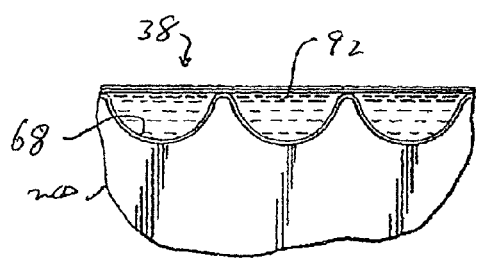
FIG. 13 is a cross-sectional view similar to FIG. 7 illustrating valleys of the staple cartridge filled with a liquid.
Figure 14:
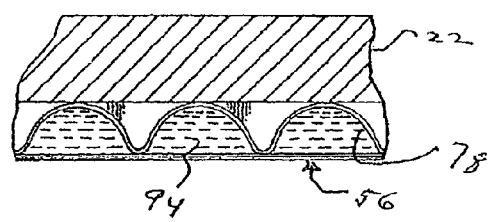
FIG. 14 is a cross-sectional view similar to FIG. 8 illustrating valleys of the anvil filled with a liquid.

In a further alternate embodiment as best shown in FIGS. 13 and 14, supply of treatment material 38 contained within depressions 68 in staple cartridge 20 may consist of a fluid 92 while supply of treatment material 56 contained within depressions 78 in anvil member 22 may also consist of a fluid 94. Fluids 92 and 94 may consist of various materials such as, for example, It is also contemplated that one treatment material could be provided in the cartridge and a different treatment material could be provided in the anvil. Alternatively, adjacent pockets in the anvil and/or in the cartridge can be formed of different material. These different materials could also be synergistic materials such that they remain separated until supplied to the tissue when they interact on contact.

Figure 15:
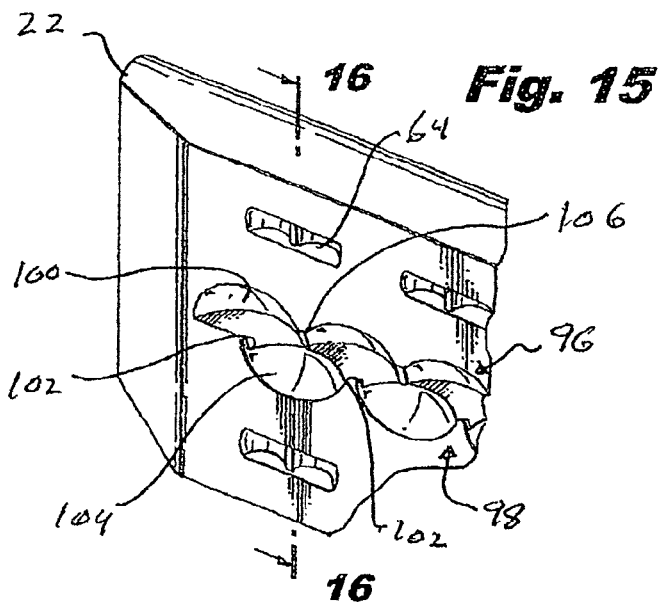
FIG. 15 is a partial perspective view of a powder containing anvil illustrating an alternative embodiment of a powder containing valley configuration.
Figure 16:
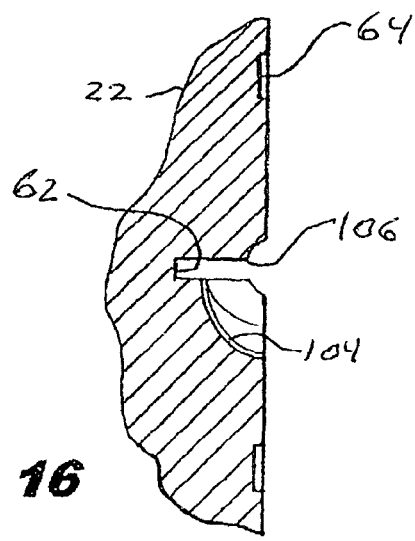
FIG. 16 is a cross-sectional view taken along line 16-16 of FIG. 15.

Referring now to FIGS. 15 and 16, there is disclosed an alternative pocket configuration for anvil member 22. Specifically, anvil member 22 is formed with rows of pockets 96 and 98 positioned on opposite sides of knife slot 62. However, unlike the pocket configurations described hereinabove, depressions 100 of pockets 96 are positioned opposite hills 102 of pockets 98 to form an opposed opposite depression\hill configuration. Similarly depressions 104 of pockets 98 are positioned opposite hills 106 of pockets 96. Thus, rather than the depressions on opposite sides of the knife slot being aligned, they are staggered so the hill on one side is aligned with a depression on the other side. This particular configuration allows the knife blade (not shown) to alternatively receive treatment materials on opposite sides from depressions 100 and 104 as it passes through knife slot 62.

Figure 17:
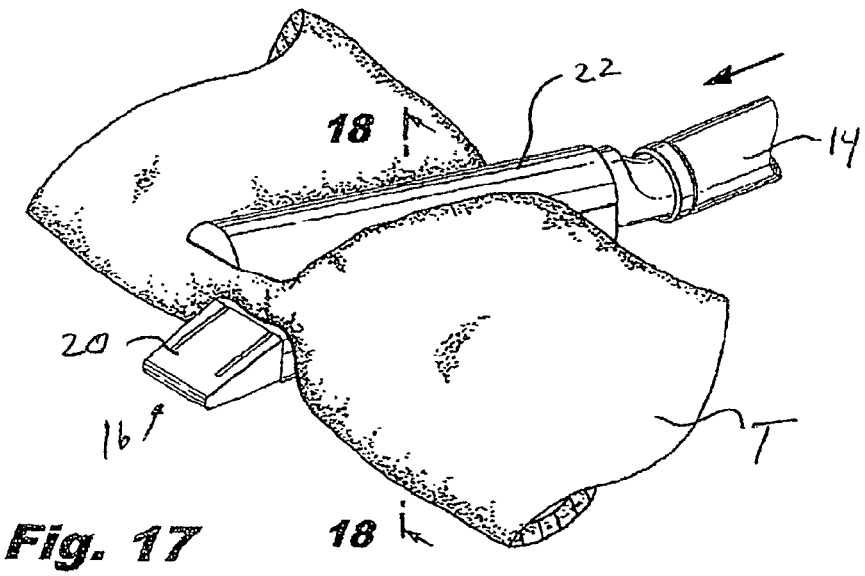
FIG. 17 is a perspective view of the distal end of the embodiment of FIG. 1 with the powder containing staple cartridge and the powder containing anvil positioned about a tissue section.
Figure 18:
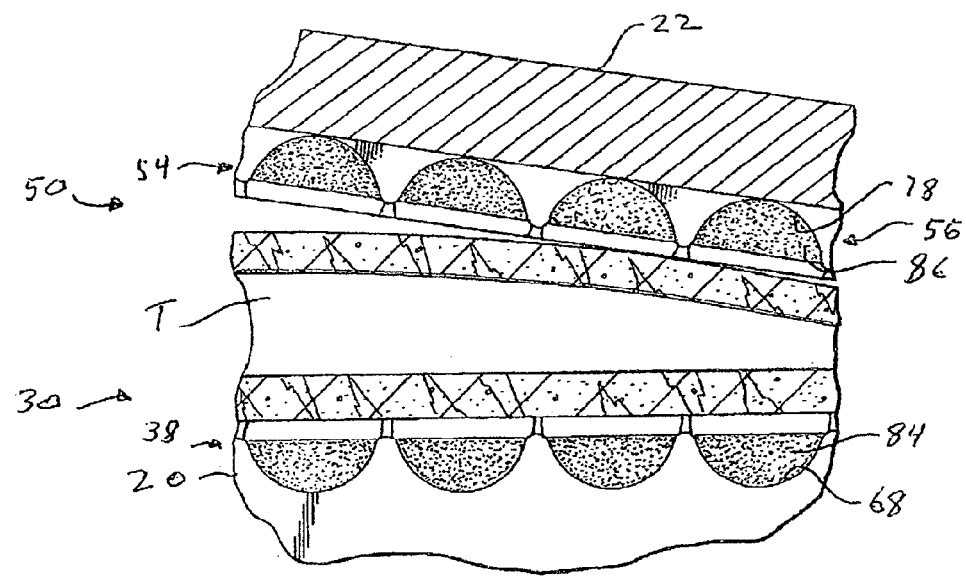
FIG. 18 is a cross-sectional view taken along the line 18-18 of FIG. 17 with the powder containing staple cartridge and the powder containing anvil in the open position about the tissue section.

Referring now to FIGS. 17-20, and initially with regard to FIGS. 17 and 18, the operation of linear stapling device 10 and, in particular, cartridge supply system 30 and anvil supply system 50 to apply treatment material to tissue during stapling and cutting will now be described. As best shown in FIG. 17, initially, jaw assembly 16 is positioned about a tissue T with anvil member 22 in the open or spaced apart position from staple cartridge 20.

Figure 19:
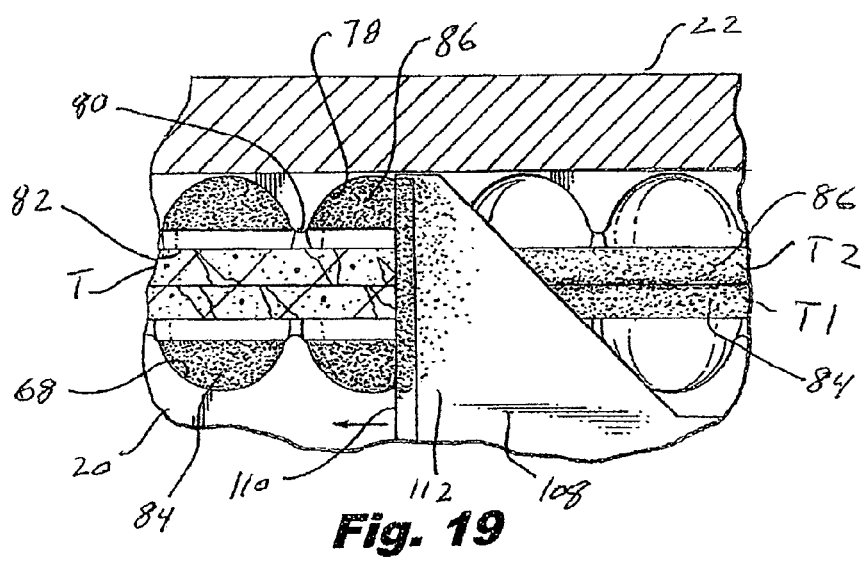
FIG. 19 is a cross-sectional view similar to FIG. 18 with the powder containing staple cartridge and the powder containing anvil in the closed position and a knife blade associated with the embodiment of FIG. 1 passing through the tissue and the powder containing valleys.

With reference to FIG. 18, cartridge supply system 30 includes treatment materials such as powder 84 positioned within depressions 68. Similarly, anvil supply system 50 includes a powdered treatment material 86 positioned within depressions 78. As shown in FIG. 19, anvil member 22 is moved to the closed position substantially adjacent to staple cartridge 20 in response to actuation of trigger 26 (FIG. 1). This clamps tissue section T between staple cartridge 20 and anvil member 22. As further shown in FIG. 19, the disclosed hills do not extend fully to the faces of anvil member 22 and staple cartridge 20. Specifically as shown with respect to anvil member 22, hill 80 does not extend completely to face 82 of anvil member 22. This can permit a slight compression of tissue section T into that area of depressions 78 not occupied by powder 86. This particular feature allows powder 86 to be applied to areas of knife blade 108 not immediately passing through tissue. Thus, leading edge 110 of knife blade 108 can continue to receive treatment material as it passes through fresh sections of tissue T.

Continued actuation of trigger 26 fires rows of staples (not shown) through tissue section T to staple tissue section T. As noted hereinabove, further actuation of trigger 26 operates to drive knife blade 108 through the knife slots in staple cartridge 20 and anvil member 22 to sever tissue section T between the applied staple lines.

As knife blade 108 moves longitudinally through the knife slots, knife blade 108 cuts tissue section T leaving cut tissue edges T1 and T2. Knife blade 108 picks up powders 84 and 86 from depressions 68 and 78 formed in staple cartridge 20 and anvil member 22 and receives powders 84 and 86 along leading edge 110 and side edges 112 of knife blade 108. Movement of knife blade 108 through tissue section T applies powders 84 and 86 to the now cut tissue edges T1 and T2. Thus, in this manner as knife blade 108 passes through tissue section T, knife blade 108 applies the desired treatment material in the form of powders 84 and 86 to the cut tissue edges T1 and T2.

Figure 20:
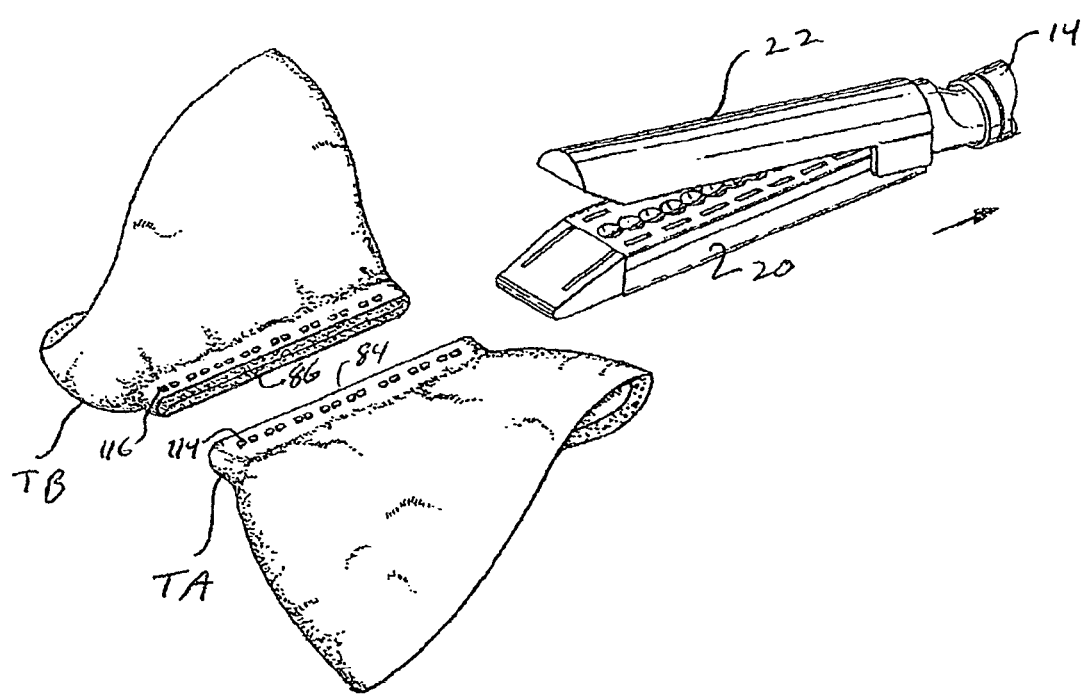
FIG. 20 is a perspective view of the segmented and stapled tissue section after the surgical stapling device of FIG. 1 has been removed.

Finally, with reference to FIG. 20, upon release of trigger 26 (FIG. 1) anvil member 22 moves to the open position spaced apart from staple cartridge 20 thereby releasing in the now cut and staple tissue sections TA and TB. As shown, the resulting tissue section TA includes a line or row of staples 114 and powder 84 while the resulting tissue section TB includes a row or staple line 116 and powder 86.

In this manner, the disclosed anvil and cartridge treatment material supply systems are configured to continuously apply a supply of treatment serial to the edges of the knife blade for application to cut tissues. As noted hereinabove, when the disclosed staple pockets are formed from the alternate configuration as illustrated in FIGS. 15 and 16, some alternate compression of the captured tissue section may occur allowing treatment material being applied to only one side of the knife blade as it cuts through a defined tissue section and alternatively to the opposite side of the knife blade as it passes through a further defined tissue section.

The endoscopic linear stapler is illustrated and described herein is one example of a surgical instrument that could be provided with the material delivery system of the present disclosure. The material delivery system could be provided with other staplers having a knife such as open linear staplers, sequential fired staples, endoluminal staplers and circular anastomotic staplers and with staplers or other devices having non-rigid, rigid, or flexible shafts.

It will be understood that various modifications may be made to the embodiments disclosed herein. For example, as noted hereinabove, the disclosed pocket and hill configurations may assume a more sinusoidal or wave shape allowing tissue to be compressed into the pockets across from hills on the opposing jaw. Further, the disclosed hill and pocket configurations are not limited to those shown, for example may be oval, elliptical, rectangular, etc. Additionally, the disclosed treatment material supply systems are not limited to the use in surgical stapling apparatus but may find application in any surgical instrument utilizing a knife blade passing through a pair of jaws to apply treatment material to cut tissues. Therefore, the above description should not be construed as limiting, but merely as exemplifications of particular embodiments. Those skilled in the art will envision other modifications within the scope and spirit of the claims appended hereto.

The invention claimed is:

1. A material deliver system of a surgical instrument having assembly including an anvil and a staple cartridge, wherein the jaw assembly defines a longitudinally extending knife slot and includes a knife, the system comprising: at least one pocket defined on a surface of the staple cartridge, the pocket being open to the knife slot, the knife slot extending through the at least one pocket such that a portion of the at least one pocket is located on each side of the knife slot; and a treatment material positioned within the at least one pocket, the knife movable within the knife slot from a retracted position to an advanced position, wherein the treatment material positioned within the at least one pocket contacts and coats the knife as the knife is advanced through the at least one pocket.

2. The material delivery system as recited in claim 1, wherein the at least one pocket includes a series of pockets defining an alternating series of depressions and hills formed in a jaw adjacent the knife slot.

3. The material delivery system as recited in claim 2, wherein the depressions have a semi-spherical configuration.

4. The material delivery system as recited in claim 2, wherein the jaw includes a tissue contacting surface and tops of the hills lie below the level of the tissue contacting surface.

5. The material delivery system as recited in claim 2, wherein the depressions positioned on a first side of the knife slot are aligned with hills positioned on a second side of the knife slot.

6. The material delivery system as recited in claim 1, wherein the treatment material is in the form of a series of plugs interconnected by stems.

7. The material delivery system as recited in claim 1, wherein the treatment material is in the form of a series of plugs interconnected by stems and defining a channel there between for passage of the knife blade.

8. The material delivery system as recited in claim 1, wherein the treatment material is in the form of a series of unconnected plugs positioned within the pockets.

9. The material delivery system as recited in claim 1, wherein the treatment material is in the form of a powder.

10. The material delivery system as recited in claim 1, wherein the treatment material is in the form of a gel.

11. The material delivery system as recited in claim 1, wherein the treatment material is in the form of a fluid.

12. The material delivery system as recited in claim 1, wherein the treatment material is in the form of a paste.

13. The material delivery system as recited in claim 1, further comprising a membrane positioned over the pockets.

14. The material delivery system as recited in claim 1, wherein the surgical instrument includes a jaw, and the at least one pocket is in the jaw, the jaw being an anvil having a plurality of staple clinching pockets.

15. A surgical stapling device comprising:
a handle having an actuator;
an elongate tubular member extending distally from the handle;
a jaw assembly positioned on a distal end of the elongate tubular member, the jaw assembly including first and second jaws movably mounted relative to each other, each of the first and second jaws having a longitudinally extending knife slot formed therein;
a knife movable from a refracted position to an advanced position within the knife slot;
a series of pockets formed on a surface of the first jaw, a portion of each of the series of pockets open to the knife slot, the knife slot extending through at least one of the series of pockets such that a portion of the at least one of the series of pockets is located on each side of the knife slot; and
a treatment material contained in the pockets, the knife contacting the treatment material contained within the pockets as the knife is moved within the pockets to the advanced position.

16. The surgical stapling device as recited in claim 15, wherein the series of pockets is formed in both the first and second jaws.

17. The surgical stapling device as recited in claim 15, wherein the series of pockets includes an alternating series of hills and depressions.

* * * * *